(12) United States Patent
Mazor et al.

(10) Patent No.: US 7,483,513 B2
(45) Date of Patent: *Jan. 27, 2009

(54) MEASUREMENT OF PROPERTIES OF THIN FILMS ON SIDEWALLS

(75) Inventors: Isaac Mazor, Haifa (IL); Boris Yokhin, Nazareth Illit (IL)

(73) Assignee: Jordan Valley Semiconductors, Ltd., Migdal Ha'emek (IL)

( * ) Notice: Subject to any disclaimer, the term of this patent is extended or adjusted under 35 U.S.C. 154(b) by 255 days.

This patent is subject to a terminal disclaimer.

(21) Appl. No.: 11/487,433

(22) Filed: Jul. 17, 2006

(65) Prior Publication Data

US 2006/0274886 A1 Dec. 7, 2006

Related U.S. Application Data

(63) Continuation of application No. 11/018,352, filed on Dec. 22, 2004, now Pat. No. 7,110,491.

(51) Int. Cl.
*G01N 23/20* (2006.01)
(52) U.S. Cl. .......................................... 378/71; 378/86
(58) Field of Classification Search ................ 378/70, 378/71, 82, 84, 86, 88, 89, 90
See application file for complete search history.

(56) References Cited

U.S. PATENT DOCUMENTS

| | | | | |
|---|---|---|---|---|
| 4,989,226 | A | 1/1991 | Woodbury et al. | 378/145 |
| 5,481,109 | A | 1/1996 | Ninomiya et al. | 250/310 |
| 5,619,548 | A | 4/1997 | Koppel | 378/70 |
| 5,740,226 | A | 4/1998 | Komiya et al. | 378/70 |
| 5,900,645 | A | 5/1999 | Yamada | 257/48 |
| 6,041,098 | A | 3/2000 | Touryanski et al. | 378/70 |
| 6,226,349 | B1 | 5/2001 | Schuster et al. | 378/84 |
| 6,381,303 | B1 | 4/2002 | Vu et al. | 378/46 |
| 6,389,102 | B2 | 5/2002 | Mazor et al. | 378/89 |
| 6,512,814 | B2 | 1/2003 | Yokhin et al. | 378/82 |
| 6,556,652 | B1 | 4/2003 | Mazor et al. | 378/86 |
| 6,639,968 | B2 | 10/2003 | Yokhin et al. | 378/70 |
| 6,750,952 | B2 | 6/2004 | Grodnensky et al. | 355/77 |
| 6,754,304 | B1 | 6/2004 | Kumakhov | 378/45 |
| 6,754,305 | B1 | 6/2004 | Rosencwaig et al. | 378/89 |
| 6,810,105 | B2 | 10/2004 | Nasser-Ghodsi et al. | 378/44 |
| 6,879,051 | B1 | 4/2005 | Singh et al. | 257/798 |
| 7,110,491 | B2 * | 9/2006 | Mazor et al. | 378/71 |
| 2001/0043668 | A1 | 11/2001 | Hayashi et al. | 378/89 |

(Continued)

OTHER PUBLICATIONS

Wiener et al., "Characterization of Titanium Nitride Layers by Grazing-Emission X-Ray Fluorescence Spectrometry", in Applied Surface Science 125 (1998), p. 129.

(Continued)

*Primary Examiner*—Courtney Thomas
(74) *Attorney, Agent, or Firm*—Smith, Gambrell & Russell, LLP (57) ABSTRACT

A method for X-ray analysis of a sample includes directing a beam of X-rays to impinge on an area of a periodic feature on a surface of the sample and receiving the X-rays scattered from the surface in a reflection mode so as to detect a spectrum of diffraction in the scattered X-rays as a function of azimuth. The spectrum of diffraction is analyzed in order to determine a dimension of the feature.

40 Claims, 6 Drawing Sheets

U.S. PATENT DOCUMENTS

2003/0128809 A1* 7/2003 Umezawa et al. ............. 378/70
2004/0156474 A1 8/2004 Yokhin et al. ................. 378/70

OTHER PUBLICATIONS

Hayashi et al., "Refracted X-Rays Propagating Near the Surface under Grazing Incidence Condition", Spectrochimica Acta, Part B 54, 1999, pp. 227-230.
Series 5000 Model XTF5011 X-Ray Tube Information, Oxford Instruments Inc., Scotts Valley, GA, U.S.A., Jun. 1998.
Monolithic Polycapillary Lens Information, X-Ray Optical Systems, Inc., Albany, NY, U.S.A., Dec. 29, 1998. (web site: www.xos.com).
S. Di Fonzo et al., "Non-Destructive Determination of Local Strain with 100-Nanometre Spatial Resolution", Nature, vol. 403, Feb. 10, 2000. (web site: www.nature.com).
Hugues Guerault, "Specular reflectivity and off-specular scattering", Tools for roughness investigation, Dec. 2000.
Jones, et al., "Small angle x-ray scattering for sub-100 nm pattern characterization", Applied Physics Letters 83:19 (2003), pp. 4059-4061.
Hu et al., "Small angle x-ray scattering metrology for sidewall angle and cross section of nanometer scale line gratings", Journal of Applied Physics 96:4 (2004), pp. 1983-1987.
Wu et al., "Small angle neutron scattering measurements of nanoscale lithographic features", Journal of Applied Physics 88:12 (2000), pp. 7298-7303.
Kojima, et al., "Structural characterization of thin films by x-ray reflectivity", Rigaku Journal 16:2 (1999), pp. 31-41.
An English abstract of JP 10 318949, Dec. 4, 1998.

* cited by examiner

MEASUREMENT OF PROPERTIES OF THIN FILMS ON SIDEWALLS

CROSS-REFERENCE TO RELATED APPLICATION

This application is a continuation of U.S. patent application Ser. No. 11/018,352, filed Dec. 22, 2004 now U.S. Pat. No. 7,110,491, of which the application is incorporated in its entirety.

FIELD OF THE INVENTION

The present invention relates generally to semiconductor manufacturing and process control, and specifically to measurements of critical dimensions of semiconductor device features.

BACKGROUND OF THE INVENTION

When microelectronic devices are produced on a semiconductor wafer, it is crucial that the critical dimensions of the devices be held within specified tolerances. Critical dimensions, in this context, refer to the widths of features, such as conductors, that are deposited on the wafer and the spacing between adjacent features. Deviations from the specified dimensions lead to performance and yield degradation. The manufacturing process must therefore be carefully monitored and controlled, in order to detect deviations as soon as they occur and to take corrective action to avoid the loss of costly wafers in process. For example, when a critical dimension in photoresist that has been deposited and etched on the wafer is found to be out of specification, it is possible to remove and reapply it.

A variety of systems and methods for measurement of critical dimensions are known in the art. Most microelectronic production facilities currently use optical metrology to monitor critical dimensions. As semiconductor devices become ever denser, however, with design rules of 0.25 μm and below, it becomes impossible For classical optical metrology systems to provide accurate results. Electron beam (e-beam) metrology has been suggested as an alternative, but e-beam systems also suffer from performance limitations.

X-ray measurement of critical dimensions is described in U.S. Pat. No. 6,556,652, whose disclosure is incorporated herein by reference. According to the method described in this patent, a surface of a substrate is irradiated with a beam of x-rays. A pattern of the X-rays scattered from the surface due to features formed on the surface is then detected and analyzed to measure a dimension of the features in a direction parallel to the surface.

Additional work on X-ray based CD measurements is described by Jones et al., in "Small Angle X-ray Scattering for Sub-100 nm Pattern Characterization," *Applied Physics Letters* 83:19 (2003), pages 4059-4061, which is incorporated herein by reference. The authors use transmission-mode small angle X-ray. scattering (SAXS) with a synchrotron X-ray source to characterize a series of polymer photoresist gratings formed on a substrate. The X-ray beam passes through the grating and the substrate, and the SAXS pattern is measured using a two-dimensional CCD detector. The photoresist grating produces a one-dimensional series of diffraction spots in the SAXS pattern on the detector. The SAXS intensity as a function of the scattering vector q is analyzed to determine the grating spacing and sidewall angle. (According to convention in the X-ray scattering art, $q = 4\pi \sin \theta/\lambda$, wherein $2\theta$ is the scattering angle relative to the Incident beam, and $\lambda$ is the X-ray wavelength.)

SUMMARY OF THE INVENTION

Embodiments of the present invention provide improved methods and apparatus for measuring dimensions of periodic features on the surface of a sample, based on detection of X-rays scattered from the surface. Typically, the scattering measurements are made in reflection mode. A beam of X-rays is directed to impinge on the area of the periodic feature, and the X-rays scattered from the surface are detected as a function of azimuth. The scattered X-rays typically exhibit a pattern of diffraction, which is analyzed in order to extract information regarding the dimensions of the periodic feature.

In some embodiments of the present invention, the sample comprises a semiconductor wafer, and the periodic feature comprises a set of lines formed on the wafer by a lithographic process, as is known in the art. The diffraction pattern is analyzed in order to determine the critical dimensions and shape of the lines on the wafer. Reflection-mode measurements, in accordance with these embodiments, afford greater signal intensity and more compact measurement geometry than the conventional transmission-mode measurements described in the above-mentioned paper by Jones et al.

In some embodiments of the present invention, X-ray diffraction measurements are used to measure characteristics of a thin film coating on the sidewalls of a periodic structure. ("Sidewalls" in this context refers to the parts of the structure that are perpendicular, or at least not parallel, to the plane of the sample surface.) In semiconductor device manufacturing, for example thin film coatings are commonly deposited over periodic structures of grooves or holes, but the thickness of the coating on the sidewalls is difficult to control precisely and difficult to measure. in these embodiments, the pattern of X-ray scattering in the azimuthal direction is analyzed in order to specifically measure the sidewall thickness and/or other sidewall characteristics. Although it is generally more convenient to measure the scattering pattern in reflection mode, as described further hereinbelow, the principles of these embodiments may alternatively be implemented in transmission mode.=

There is therefore provided, in accordance with an embodiment of the present invention, a method for X-ray analysis of a sample, including:

directing a beam of X-rays to impinge on an area of a periodic feature on a surface of the sample;

receiving the X-rays scattered from the surface in a reflection mode so as to detect a spectrum of diffraction in the scattered X-rays as a function of azimuth; and analyzing the spectrum of diffraction in order to determine a dimension of the feature.

Typically, directing the beam includes collimating the beam of X-rays that is to impinge on the surface.

In disclosed embodiments, directing the beam includes directing the beam to impinge on the surface at a grazing angle, and receiving the X-rays includes detecting a variation in the scattered X-rays associated with total external reflection from the area of the surface. In some of these embodiments, the periodic feature includes a layer having a first critical angle, formed over a substrate having a second critical angle, and directing the beam Includes directing the beam at an angle between the first and second critical angles. In one embodiment, the layer includes an organic material, and the substrate includes at least one of a metal, a semiconductor and a dielectric material.

In some embodiments, the feature a pattern of parallel linear elements, and analyzing the spectrum includes measuring a separation between side lobes in the spectrum in order to determine a spacing between the parallel lines.

In further embodiments, the feature includes sidewalls, which are overlaid with a thin film, and analyzing the spectrum includes measuring a thickness of the thin film on the sidewalls.

In a disclosed embodiment, the sample includes a semiconductor wafer, and the periodic feature includes photoresist deposited on the surface.

There is also provided, in accordance with an embodiment of the present invention, a method for X-ray analysis of a sample, including:

directing a beam of X-rays to impinge on an area of a planar sample that includes a feature having sidewalls perpendicular to a plane of the sample, the sidewalls having a thin film thereon;

detecting a spectrum of the X-rays scattered from the sample due to the feature; and analyzing the spectrum to measure a characteristic of the thin film on the sidewalls.

In some embodiments, the feature includes a periodic pattern, and analyzing the spectrum includes analyzing a diffraction spectrum due to the periodic pattern. Typically, the diffraction spectrum includes multiple side lobes, and analyzing, the diffraction spectrum includes observing a modulation of the side lobes as a function of angle. in one embodiment, observing the modulation includes determining a thickness of the thin film responsively to an angular spacing of the side lobes.

In a disclosed embodiment, the sample includes a semiconductor wafer, and the thin film includes a barrier layer.

There is additionally provided, in accordance with an embodiment of the present invention, apparatus for X-ray analysis of a sample having a periodic feature on a surface thereof, the apparatus including:

an X-ray source, which is adapted to direct a beam of X-rays to impinge on an area of the surface containing the periodic feature;

a detector, which is adapted to receive the X-rays scattered from the surface in a reflection mode so as to detect a spectrum of diffraction in the scattered X-rays as a function of azimuth; and a signal processor, which is adapted to analyze the spectrum of diffraction in order to determine a dimension of the feature.

There is further provided, in accordance with an embodiment of the present invention, apparatus for X-ray analysis of a planar sample that includes a feature having sidewalls perpendicular to a plane of the sample, the sidewalls having a thin film thereon, the apparatus including:

an X-ray source, which is adapted to direct a beam of X-rays to impinge on an area of the sample containing the feature;

a detector, which is adapted to detect a spectrum of the X-rays scattered from the sample due to the feature; and a signal processor, which is adapted to analyze the spectrum to measure a characteristic of the thin film on the sidewalls.

There is moreover provided, in accordance with an embodiment of the present invention, a cluster tool for producing microelectronic devices, including:

a fabrication station, which is adapted to form a periodic feature on a surface of a semiconductor wafer; and an inspection station, including:

an X-ray source, which is adapted to direct a beam of X-rays to impinge on an area of the surface containing the periodic feature;

a detector, which is adapted to receive the X-rays scattered from the surface in a reflection mode so as to detect a spectrum of diffraction in the scattered X-rays as a function of azimuth; and a signal processor, which is adapted to analyze the spectrum of diffraction in order to determine a dimension of the feature.

There is furthermore provided, in accordance with an embodiment of the present invention, apparatus for producing microelectronic devices, including:

a production chamber, which is adapted to receive a semiconductor wafer;

a fabrication device, which is adapted to form a periodic feature on a surface of the semiconductor wafer within the chamber;

an X-ray source, which is adapted to direct a beam of X-rays toward the semiconductor wafer in the production chamber so as to impinge on an area of the surface containing the periodic feature;

a detector, which is adapted to receive the X-rays scattered from the surface in a reflection mode so as to detect a spectrum of diffraction in the scattered X-rays as a function of azimuth; and a signal processor, which is adapted to analyze the spectrum of diffraction in order to determine a dimension of the feature.

The present invention will be more fully understood from the following detailed description of the embodiments thereof, taken together with the drawings in which:

DETAILED DESCRIPTION OF EMBODIMENTS

Figure 1:
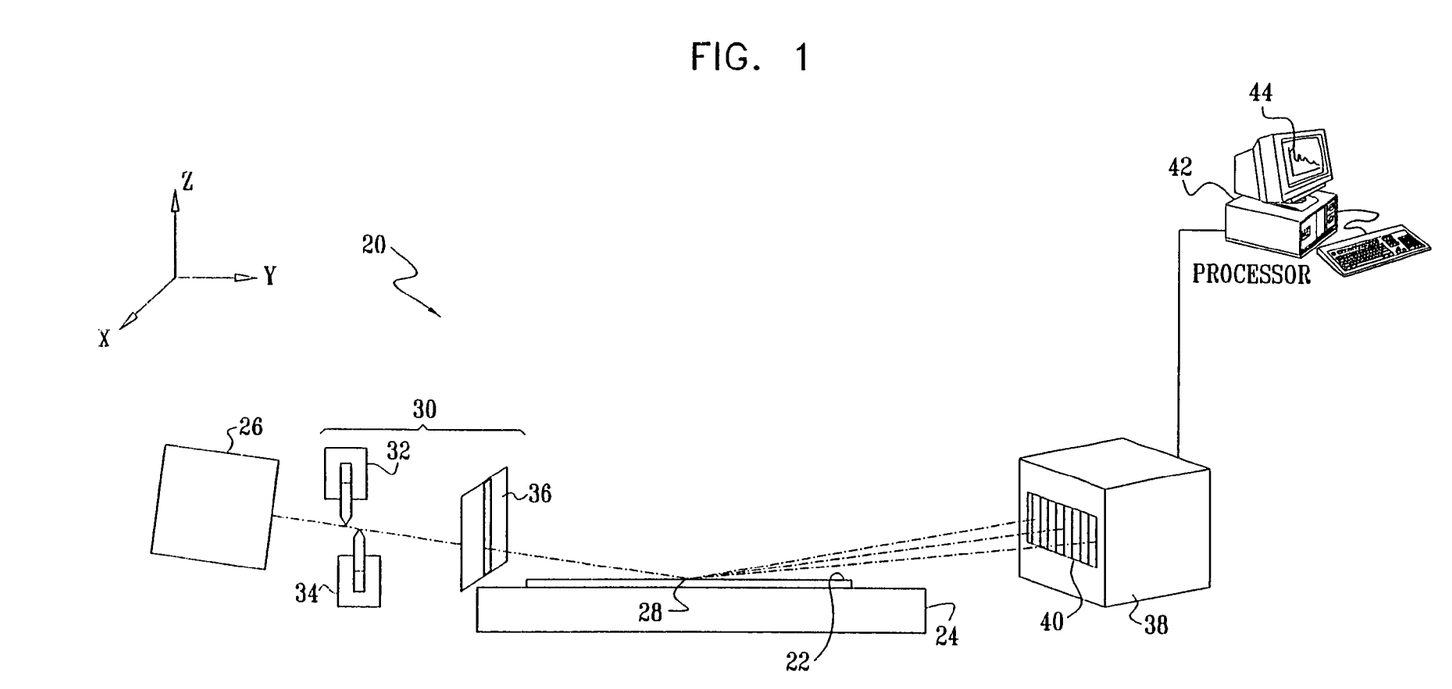
FIG. 1 is a schematic side view of apparatus for measurement of critical dimensions using X-rays, in accordance with an embodiment of the present invention.

FIG. 1 is a schematic, pictorial illustration of a system 20 for measurement of critical dimensions on a semiconductor wafer 22, in accordance with an embodiment of the present invention. An X-ray source 26 emits a beam of X-rays, which is collimated by collimating optics 30 and directed onto a target area 28 on wafer 22. The wafer is typically mounted on a motion stage 24, which moves the wafer so that target area 28 may be scanned to different points on the wafer surface. Although the embodiments described hereinbelow relate specifically to wafer 22, the principles of the present invention may similarly be applied to other patterned samples.

X-ray source 26 typically comprises an X-ray tube with monochromatizing optics (not shown in the figures). For example, the X-ray tube may be an XTF 5011 tube produced by Oxford Instruments, Inc. (Scotts Valley, Calif.). A number of different types of monochromatizing optics that may be used in system 20 are described in U.S. Pat. No. 6,381,303, whose disclosure is incorporated herein by reference. For example, the optics may comprise a curved crystal monochromator, such as the Doubly-Bent Focusing Crystal Optic, produced by XOS Inc., of Albany, N.Y. Other suitable optics are described in U.S. Pat. No. 5,619,548, whose disclosure is likewise incorporated herein by reference.

Collimating optics 30 may generally comprise any suitable X-ray collimating means known In the art. in the present example, optics 30 comprise an adjustable knife edge 32 and shutter 34, which control the vertical (Z-direction) angle and extent of the X-ray beam. A slit 36, whose width may also be variable, controls the horizontal (X-direction) angle and extent of the beam. For the sake of convenience, as shown in FIG. 1, the Y-direction is taken to be the projection of the axis of the incident beam onto the X-Y plane (i.e., onto the surface of wafer 22). Alternatively or additionally, collimating optics 30 may comprise one or more pinholes or suitable reflective elements, for example.

Radiation scattered from wafer 22 is collected by an X-ray detector 38. System 20 operates in reflection mode, i.e., detector 38 is located on the same side of the sample plane as source 26. (By contrast, in the transmission mode described in the above-mentioned article by Jones et al., the X-ray source and detector are on opposite sides of the sample, so that scattered X-rays are detected after passing through the entire width of the sample.) Typically, detector 38 comprises an array 40 of X-ray detecting elements, such as a CCD array. Alternatively, other types of X-ray detectors may be used in this context, as are known in the art. The array detector is advantageous in being able to simultaneously receive and measure the scattered radiation over a range of azimuthal angles. (In the context of the present patent application and in the claims, the terms "azimuth" and "azimuthal" refer to the angle about the Z-axis, i.e., an angle in a plane parallel to the X-Y plane of wafer 22.) The scattered radiation exhibits a diffraction spectrum 44 in the azimuthal direction that is characteristic of the critical dimensions of a periodic pattern in area 28, as described further hereinbelow.

Detector 38 outputs a signal responsive to the flux of X-ray photons incident on the detector. The signal is received and analyzed by a signal processor 42, preferably a general-purpose computer equipped with suitable signal processing hardware and software. The processor analyzes the diffraction spectrum of the scattered radiation and outputs a measurement of selected critical dimensions of the pattern on wafer 22.

Figure 2:
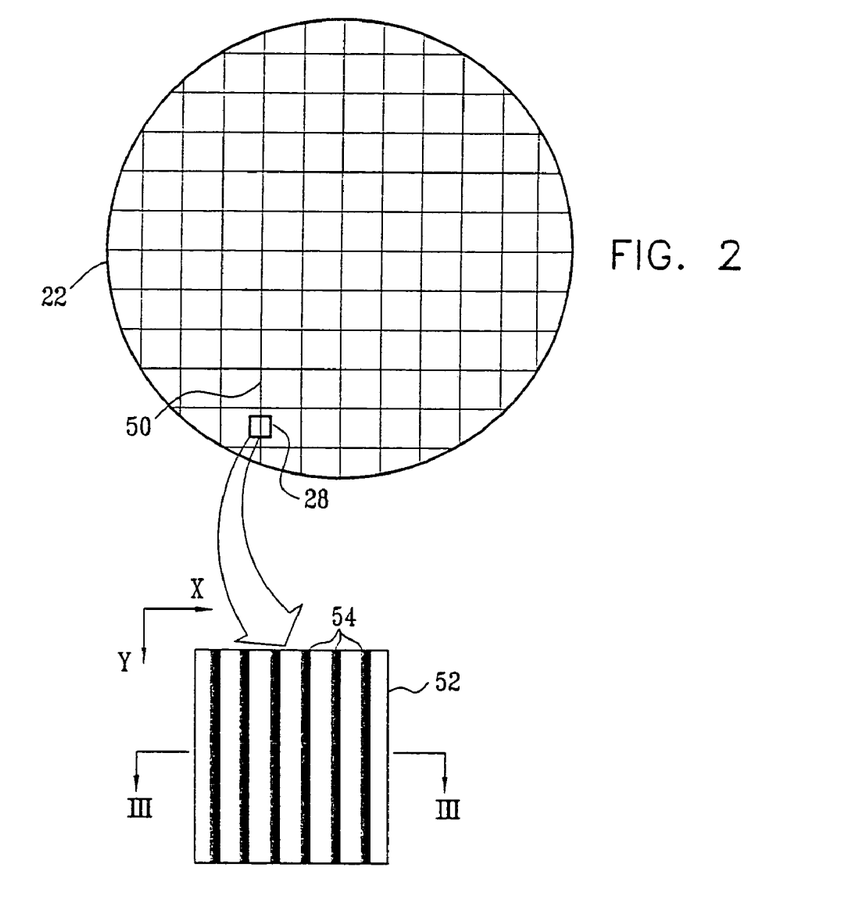
FIG. 2 is a schematic top view of a semiconductor wafer and a detail of a periodic pattern on the wafer.
Figure 3:
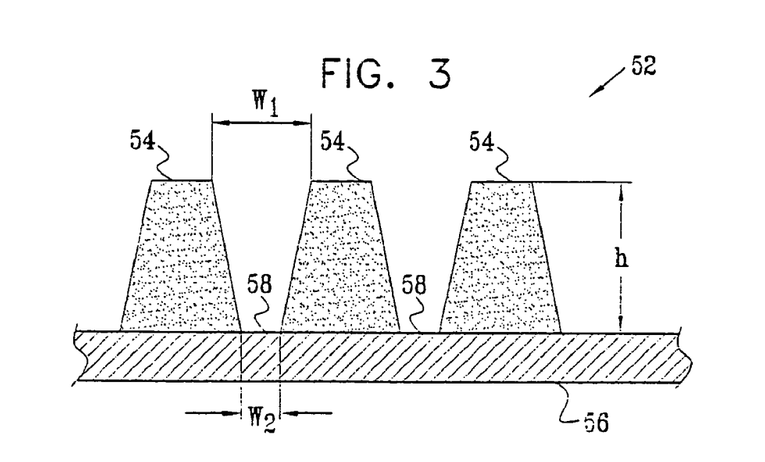
FIG. 3 is a schematic, cross-sectional view of the test pattern of FIG. 2, taken along a line III-III.

Reference is now made to FIGS. 2 and 3, which schematically show details wafer 22, and specifically a periodic pattern 52 formed thereon. FIG. 2 is a top view of the wafer, with pattern 52 shown enlarged in an inset, while FIG. 3 is an enlarged, cross-sectional view of the test pattern, taken along line III-III in FIG. 2. Pattern 52 in this example comprises a grating of parallel linear elements, such as ridges 54, which are assumed to be aligned along the Y-direction. Pattern 52 may be a special test pattern, which is formed on a scribe line 50 between adjacent dies on wafer 22 for use in CD measurement. In this case, ridges 54 are typically formed by the same processes of material deposition, photolithography and etching as are functional circuit features on the wafer that pattern 52 is intended to test. Alternatively, pattern 52 may comprise an actual, functional pattern within the dies on the wafer.

In the example of FIGS. 2 and 3, ridges 54 comprise photoresist. The photoresist is masked and etched to form gaps 58 between the ridges. Within gaps 58, an underlying substrate layer 56 is exposed. Layer 56 typically comprises an oxide or metal layer, or it may comprise the silicon wafer substrate itself. In modern devices, the height h of ridges 54 is typically five to six times the width of gaps 58. Because of this high aspect ratio and the nature of the chemical etching process used to create gaps 58, the widths of the gaps are generally not uniform. Rather, the widths tend to have a larger dimension $W_1$ at the upper surface of ridges 54, and a smaller dimension $W_2$ at the bottom of the gaps. The methods of measurement described hereinbelow are capable of measuring the slope of the sidewalls of ridges 54, and thus can give both $W_1$ and $W_2$.

The X-ray beam that is output by collimating optics 30 impinges on area 28 at a grazing angle, i.e., nearly parallel to the surface plane. In order to observe diffraction pattern 44 at detector 38, it is desirable that the X-ray beam be incident on pattern 52 at an angle below the critical angle of substrate layer 56 for total external reflection, but above the smaller critical angle of the photoresist making up ridges 54. Assuming substrate layer 56 to comprise silicon, and ridges 54 to comprise an organic photoresist, the incident angle for a CuKa (8.05 kev) X-ray beam should then be between about 0.15° and 0.23°. At this low angle, the X-ray beam will be incident on the surface of wafer 22 over an elongated spot—with the spot length in the Y-direction much greater than the width in the X-direction. For example, if the width of the beam exiting collimating optics 30 is 80 μm, the spot on wafer 22 will be about 80 μm wide by 20-30 mm long. It is thus advantageous that pattern 52 on wafer 22 be at least this long. In this case, the incident X-ray beam will interact with the pattern on the surface over a large area, resulting in a diffraction spectrum 44 with relatively high contrast.

Figure 4:
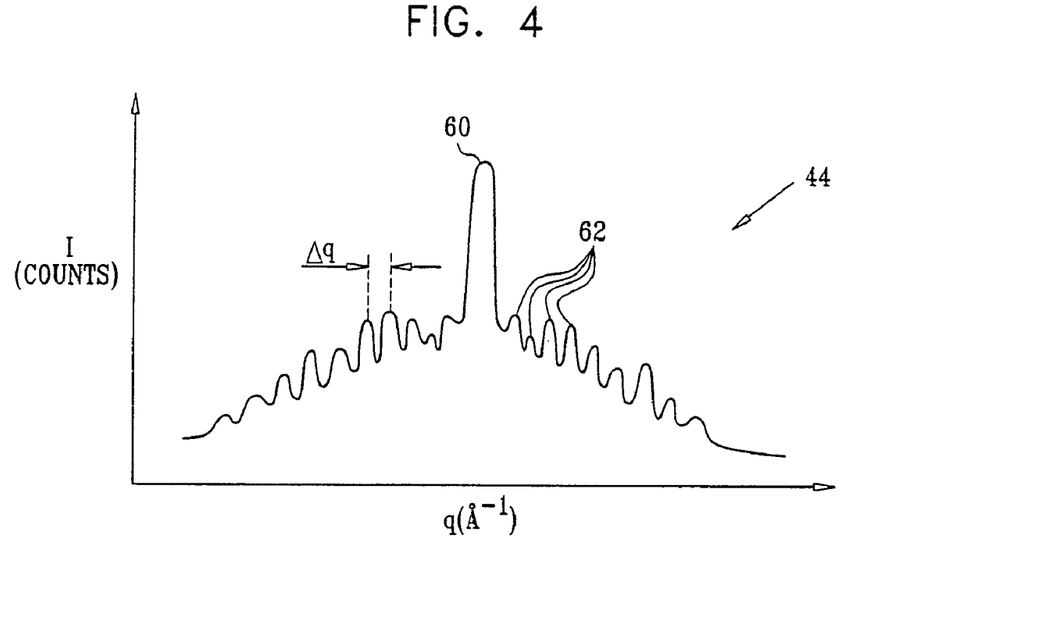
FIG. 4 is a schematic plot of scattering intensity as a function of the scattering vector q, in accordance with an embodiment of the present invention.

FIG. 4 is a schematic plot of scattering intensity showing diffraction spectrum 44 produced in system 20, in accordance with an embodiment of the present invention.

The azimuthal angular measure provided by array 40 is translated into scattering vector units q, as defined above. Spectrum 44 comprises a strong, zero-order peak 60, with side lobes 62 corresponding to the higher diffraction orders. By the basic principles of diffraction, the spacing of lobes 62 is simply $\Delta q = 2\pi/L$, wherein L is the period of pattern 52. For example, for L=130 nm, the lobe spacing is $\Delta q = 0.005$ Å$^{-1}$, which corresponds to 0.068° for the above-mentioned CuKa X-ray line. Assuming array 40 to have a pitch between detector elements of about 25 μm and to be located 30-40 cm from area 28 on wafer 22, pattern 44 will be well-resolved by detector 38.

To minimize blur, and thus maximize contrast, in the detection of spectrum 44, it is desirable to limit the angular spread of the X-ray beam that is incident on wafer 22. Generally speaking, the angular spread should be reduced to the minimum possible value that will still give adequate count rate (throughput) and signal/noise ratio at detector 38. Practically speaking, in system 20, this means that collimating optics 30 should typically be adjusted to limit the beam divergence to no more than about 0.1° in both the horizontal (X) and vertical (Z) directions. These are empirical figures, however, and the optimal settings for any given measurement setup may be determined by a simple trial-and-error adjustment process. To permit such adjustments, it is desirable that the angular range of collimating optics 30 be variable in steps of 0.01° or less, in both the horizontal and vertical directions.

The width $W_1$ and the sidewall angle of gaps 58 (FIG. 3) may be derived from the relative heights of side lobes 62 in spectrum 44. For this purpose, a mathematical model of the scattering spectrum of pattern 52, including the gap width and sidewall angle as parameters, is fitted to the measured diffraction spectrum 44. The parameters that give the optimal fit are indicative of the actual parameters of pattern 52. Methods for performing this sort of fitting are described, for example, by Hu et al., in "Small Angle X-ray Scattering Metrology for Sidewall Angle and Cross Section of Nanometer Scale Line Gratings," *Journal of Applied Physics* 96:4 (2004), pages 1983-1987, and by Wu et al., in "Small Angle Neutron Scattering Measurements of Nanoscale Lithographic Features," *Journal of Applied Physics* 88:12 (2000), pages 7298-7303. Both of these publications are incorporated herein by reference.

Figure 5:
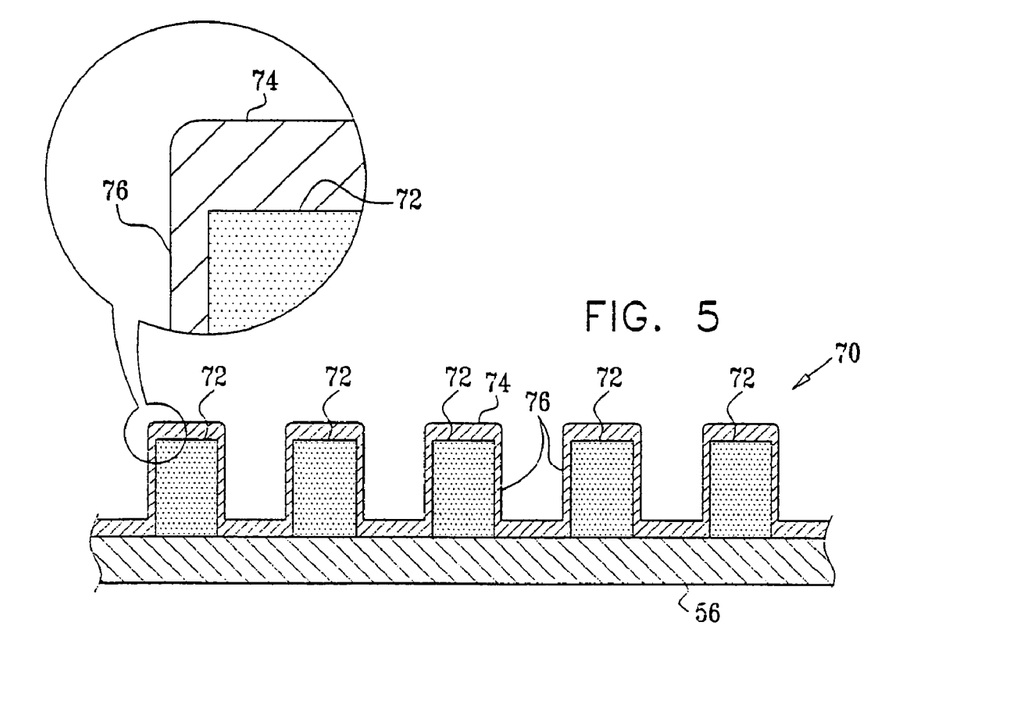
FIG. 5 is a schematic, sectional view of a periodic pattern on a sample surface, which is overlaid by a thin film layer.

FIG. 5 is a schematic, sectional illustration of a pattern 70 formed on substrate layer 56, whose characteristics are measured by means of X-ray scattering in accordance with another embodiment of the present invention. In this embodiment, pattern 70 comprises ridges 72, which are overlaid by a thin film layer 74. For example, layer 74 may comprise a diffusion barrier, which is deposited over ridges 72 of oxide or semiconductor material before filling the gaps between the ridges with metal. The process by which layer 74 is deposited over pattern 70 must be carefully controlled so that she thickness of the layer is within the predefined process bounds, typically 10-20 Å. In practice, however, because of the geometry of the wafer and the deposition equipment, the thickness of the layer that is deposited on sidewalls 76 of ridges 72 is typically less than the thickness on the horizontal surfaces at the top and bottom of the ridges. It is therefore particularly important to measure the sidewall layer thickness.

Figure 6:
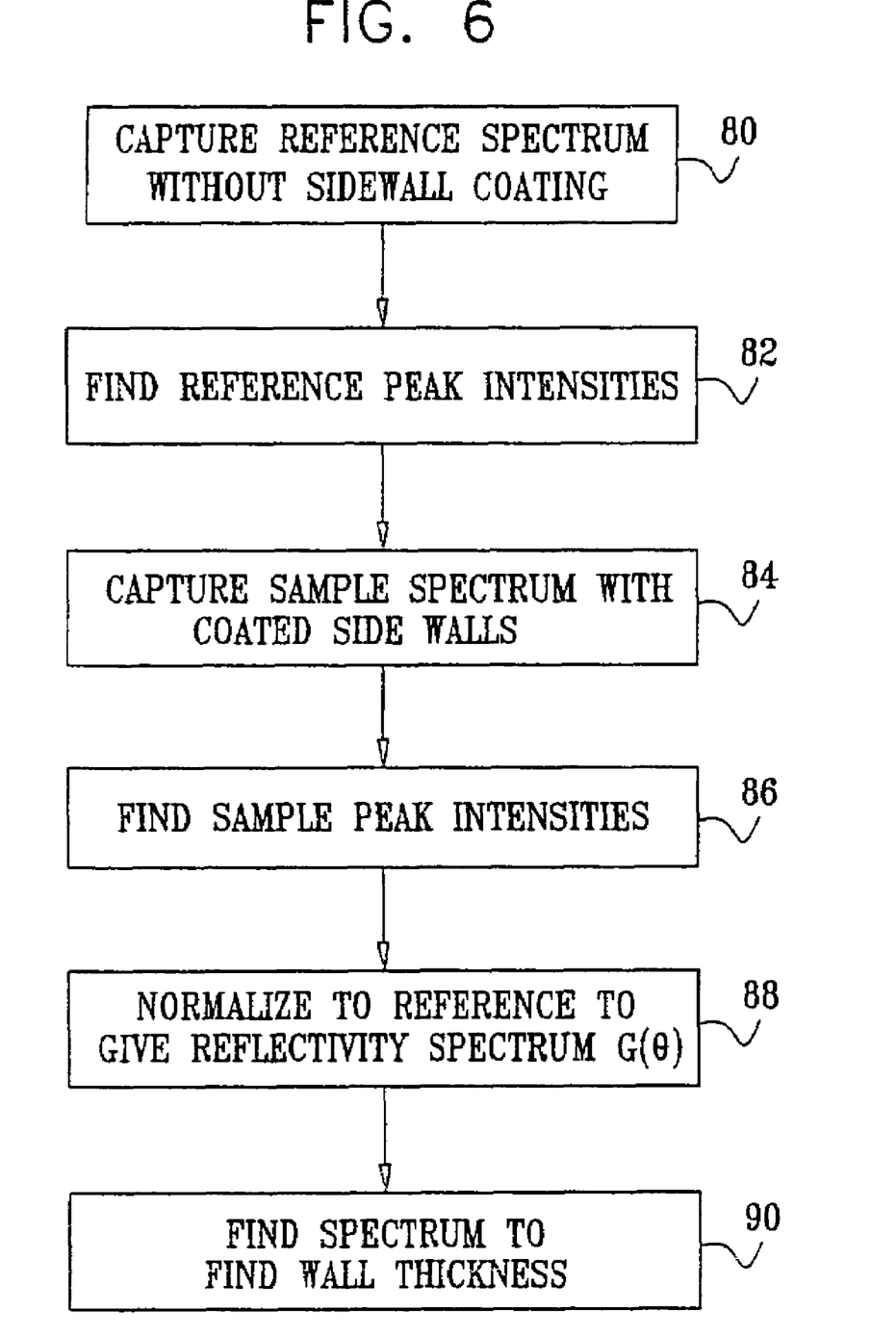
FIG. 6 is a flow chart that schematically illustrates a method for measuring sidewall thickness of a thin film layer, in accordance with an embodiment of the present invention.

FIG. 6 is a flow chart that schematically illustrates a method for measuring sidewall layer thickness in system 20, in accordance with an embodiment of the present invention. The thickness measurement is derived from variations in the relative intensities of side lobes 62 in diffraction spectrum 44. In order to make the measurement, a reference sample with pattern 70 but without layer 74 formed on the sidewalls of the pattern is placed in area 28, at a reference capture step 80. Processor 42 captures a reference diffraction spectrum using the reference sample. The processor analyzes this spectrum to locate lobes 62, and records the peak intensities of the lobes, at a peak location step 82. The peak intensities for the first N side lobes (averaged over the left and right sides of the diffraction pattern, which should be symmetrical) are stored in an array f[k], wherein k=1, ..., N.

Now the actual sample with pattern 70, including layer 74 on sidewalls 76, is placed in area 28, and processor 42 captures the diffraction spectrum of the sample, at a sample capture step 84. The processor records the peak intensities of the side lobes in this spectrum, at a peak measurement step 86, and stores the peak intensities in a corresponding array F[k]. The spacing $\Delta q$ of the side lobes in this diffraction spectrum should be the same as that in the reference spectrum, and any changes in the peak intensities of the side lobes can be attributed to the effect of Layer 74. Therefore, processor 42 uses the stored reference array f[k] to normalize the sample peak measurement, at a normalization step 88, giving a normalized array of peak intensities G[k]=F[k]/f[k], which isolates the effects of layer 74 on the diffraction spectrum.

Each peak order k in G[k] is associated with the corresponding azimuthal angle θ (equal to the angular displacement of the corresponding lobe 62 from central peak 60), giving a spectrum G(θ) as a function of the diffraction angle. G(θ) is a reflectivity spectrum, in the sense that the variation of the peak intensities of the side lobes with θ (after normalization at step 88) depends on the reflection properties of sidewalls 76. This property is explained further with reference to the figure that follows.

Figure 7:
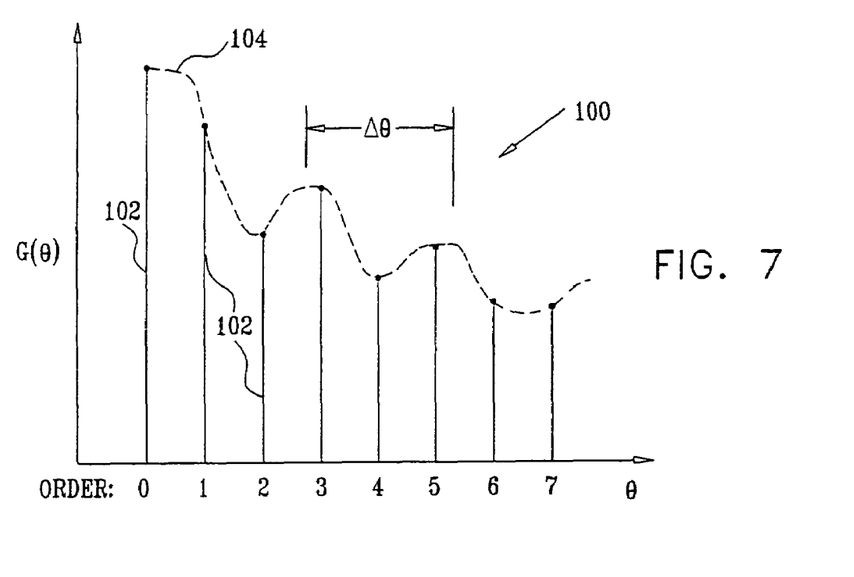
FIG. 7 is a schematic plot of the intensity of a sequence of diffraction orders, in accordance with an embodiment of the present invention.

FIG. 7 is a schematic plot showing a reflectivity spectrum 100, G(θ), which is produced by system 20 using the method of FIG. 6, in accordance with an embodiment of the present invention. Vertical bars 102 represent the values of G(θ) for diffraction orders k=0, 1, 2, .... The values vary with angle in an oscillatory modulation pattern, with period $\Delta\theta$. The oscillation is due to the interference of X-rays reflected from the outer surface of layer 74 on sidewalls 76 with the X-rays that are reflected from the vertical sides of ridges 72 underneath layer 74. The period $\Delta\theta$ is determined by the thickness of layer 74 on the sidewalls.

Spectrum 100 is thus analogous to an X-ray reflectivity (XRR) spectrum, as described, for example, in U.S. Pat. Nos. 6,512,814 and 6,639,968, whose disclosures are incorporated herein by reference. (Such spectra, however, are normally measured and analyzed as a function of elevation angle, while spectrum 100 is measured and analyzed as a function of the azimuthal angle.) XRR spectra contain oscillatory patterns, which are indicative of properties of thin film layers formed on the surface of a sample. As described in the above-mentioned patents, a parametric model may be fitted to XRR spectra in order to derive properties of the thin film layers, including thickness, density and surface quality. Similarly, in the present case, processor 42 fits a curve 104 to spectrum 100, at a fitting step 90 (FIG. 6). Methods for performing this sort of fitting are known in the XRR art, as described, for example, by Kojima et al., in "Structural Characterization of Thin Films by X-ray Reflectivity," *Rigaku Journal* 16:2 (1999), pages 31-41, which is incorporated herein by reference. The frequency of oscillation of curve 104 (i.e., $1/\Delta\theta$) is proportional to the thickness of layer 74 on sidewalls 76. Processor 42 thus uses curve 104 in order to determine whether this thickness is within the desired range.

Figure 8:
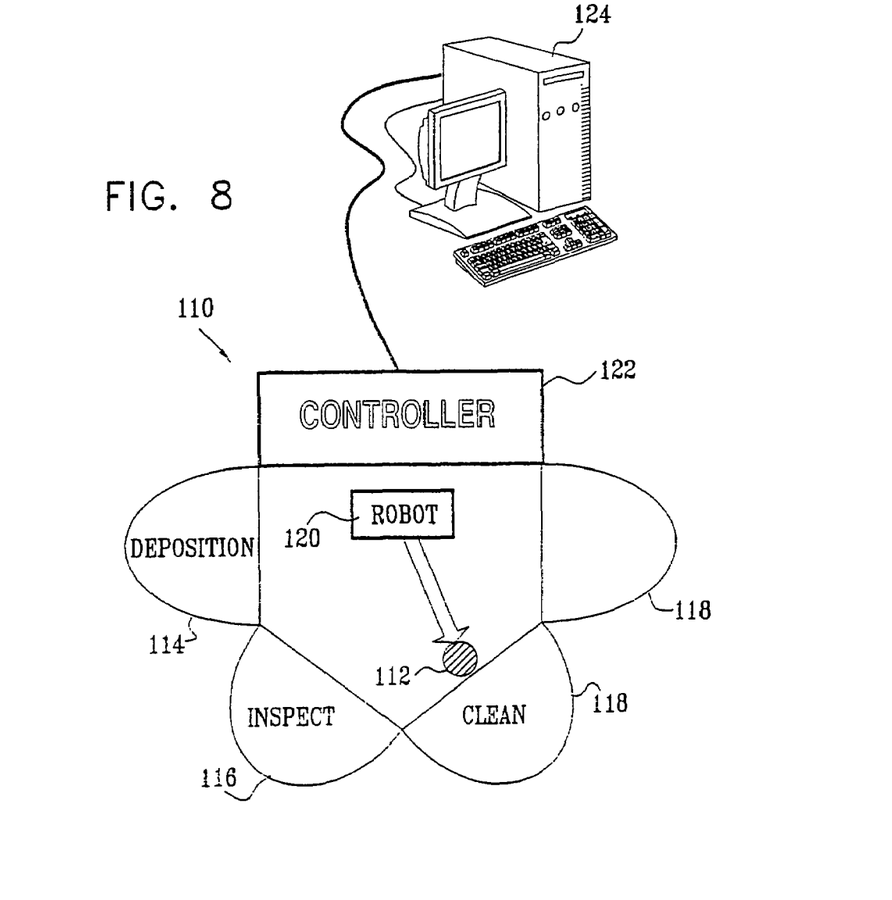
FIG. 8 is a schematic top view of a cluster tool for semiconductor device fabrication, including an inspection station in accordance with an embodiment of the present invention.

FIG. 8 is a schematic top view of a cluster tool 110 for use in semiconductor device fabrication, in accordance with an embodiment of the present invention. The cluster tool comprises multiple stations, including a deposition station 114, for depositing thin films on a semiconductor wafer 112, an inspection station 116, and other stations 118, as are known in the art, such as a cleaning station. Inspection station 116 is constructed and operates in a manner similar to system 20; as described hereinabove. A robot 120 transfers wafer 112 among stations 114, 116, 118, ..., under the control of a system controller 122. Operation of tool 110 may be controlled and monitored by an operator using a workstation 124, coupled to controller 122.

Inspection station 116 is used to perform critical dimension measurements on wafer 112, typically by means of reflection-mode X-ray scattering. Such measurement is carried out before and/or after selected steps in production processes performed by deposition station 114 and other stations in tool 110. Use of station 116 allows early detection of process deviations and convenient adjustment and evaluation of process parameters on production wafers, using controller 122 and possibly workstation 124.

Figure 9:
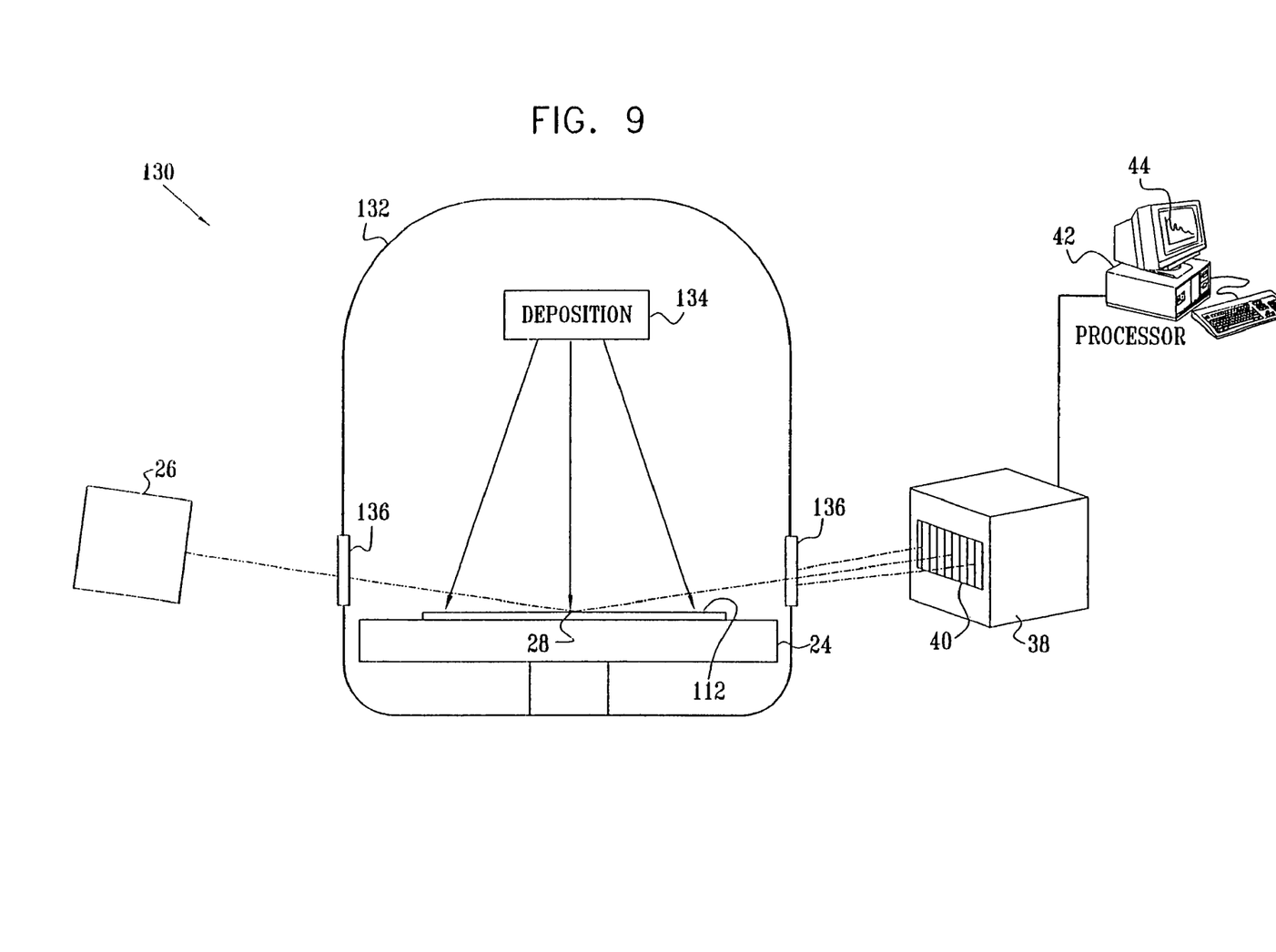
FIG. 9 is a schematic side view of a semiconductor processing chamber with X-ray inspection capability, in accordance with an embodiment of the present invention.

FIG. 9 is a schematic side view of a system 130 for semiconductor wafer fabrication and in situ inspection, in accordance with another embodiment of the present invention.

System 130 comprises a vacuum chamber 132, containing deposition apparatus 134, for creating thin films on wafer 112, as is known in the art. The wafer is mounted on motion stage 24 within chamber 132. The chamber typically comprises X-ray windows 136. These windows may be of the type described in U.S. Patent application Publication US 2001/0043668 A1, whose disclosure is incorporated herein by reference. X-ray source 26 irradiates area 28 on wafer 112 via one of windows 136, in the manner described above. Some of the elements shown in FIG. 1 are omitted from FIG. 9 for the sake of simplicity, but typically, elements of this sort are integrated into system 130, as well.

X-rays scattered from area 28 are received by array 40 in detector assembly 38 via another one of windows 136. Processor 42 receives signals from detector assembly 38, and processes the signals in order to assess critical dimensions of features in production within chamber 132, by measuring X-ray scattering from wafer 112. The results of the critical dimension measurement may be used in controlling deposition apparatus 134 so that the films produced by system 130 have desired dimensions.

Although the embodiments described above refer specifically to X-ray scattering, the principles of the present invention may similarly be used, *mutatis mutandis*, in other fields of X-ray analysis. Exemplary fields of application include X-ray fluorescence (XRF) analysis, including particularly grazing emission XRF, as well as other XRF techniques known in the art. Grazing emission XRF is described, for example, in an article by Wiener et al., entitled "Characterization of Titanium Nitride Layers by Grazing-Emission X-ray Fluorescence Spectrometry," in *Applied Surface Science* 125 (1998), p. 129, which is incorporated herein by reference. X-ray fluorescence measurement may be incorporated in system 20, as described in the above-mentioned U.S. Pat. No. 6,381,303, for example. Additionally or alternatively, the system may be adapted for A-ray reflectometry, as well as small-angle scattering measurements, as described in U.S. patent application Ser. No.10/364,883, published as US 2004/0156474 A1, whose disclosure is incorporated herein by reference. Further additionally or alternatively, system 20 may be adapted for other types of X-ray diffraction measurements. Furthermore, the principles of system 20 may be implemented in position-sensitive detection systems for other energy ranges, such as for detection of gamma rays and other nuclear radiation.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for X-ray analysis of a sample, comprising:
   directing a beam of X-rays to impinge on an area of a periodic feature on a surface of the sample;
   receiving the X-rays scattered from the surface in a reflection mode so as to detect a spectrum of diffraction in the scattered X-rays as a function of azimuth; and
   analyzing the spectrum of diffraction by measuring respective intensities of side lobes at different angles in the spectrum in order to determine a dimension of the feature.

2. The method according to claim 1, wherein directing the beam comprises collimating the beam of X-rays that is to impinge on the surface.

3. The method according to claim 1, wherein directing the beam comprises directing the beam to impinge on the surface at a grazing angle, and wherein receiving the X-rays comprises detecting a variation in the scattered X-rays associated with total external reflection from the area of the surface.

4. The method according to claim 3, wherein the periodic feature comprises a layer having a first critical angle formed over a substrate having a second critical angle, and wherein directing the beam comprises directing the beam at an angle between the first and second critical angles.

5. The method according to claim 4, wherein the layer comprises an organic material, and the substrate comprises at least one of a metal, a semiconductor and a dielectric material.

6. The method according to claim 1, wherein the feature comprises a pattern of parallel linear elements, and wherein analyzing the spectrum comprises measuring a separation between side lobes in the spectrum in order to determine a spacing between the parallel lines.

7. The method according to claim 1, wherein the feature comprises sidewalls, which are overlaid with a thin film, and wherein analyzing the spectrum comprises measuring a thickness of the thin film on the sidewalls.

8. The method according to claim 1, wherein the sample comprises a semiconductor wafer.

9. The method according to claim 8, wherein the periodic feature comprises photoresist deposited on the surface.

10. The method according to claim 1, wherein analyzing the spectrum comprises observing analyzing a modulation of the intensities of the side lobes as a function of angle.

11. A method for X-ray analysis of a sample, comprising:
    directing a beam of X-rays to impinge on an area of a planar sample that comprises a feature having sidewalls perpendicular to a plane of the sample, the sidewalls having a thin film thereon;
    detecting a spectrum of the X-rays scattered from the sample due to the feature; and
    analyzing the spectrum to measure a characteristic that is specific to the thin film on the sidewalls.

12. The method according to claim 11, wherein directing the beam comprises collimating the beam of X-rays that is to impinge on the surface.

13. The method according to claim 11, wherein directing the beam comprises directing the beam to impinge on the surface at a grazing angle, and wherein receiving the X-rays comprises detecting a variation in the scattered X-rays associated with total external reflection from the area of the surface.

14. The method according to claim 11, wherein the feature comprises a periodic pattern, and wherein analyzing the spectrum comprises analyzing a diffraction spectrum due to the periodic pattern.

15. The method according to claim 14, wherein the diffraction spectrum comprises multiple side lobes, and wherein analyzing the diffraction spectrum comprises observing a modulation of the side lobes as a function of angle.

16. The method according to claim 15, wherein observing the modulation comprises determining a thickness of the thin film responsively to an angular spacing of the side lobes.

17. The method according to claim 11, wherein the sample comprises a semiconductor wafer.

18. The method according to claim 17, wherein the thin film comprises a barrier layer.

19. Apparatus for X-ray analysis of a sample having a periodic feature on a surface thereof, the apparatus comprising:
- an X-ray source, which is adapted to direct a beam of X-rays to impinge on an area of the surface containing the periodic feature;
- a detector, which is adapted to receive the X-rays scattered from the surface in a reflection mode so as to detect a spectrum of diffraction in the scattered X-rays as a function of azimuth; and
- a signal processor, which is adapted to analyze the spectrum of diffraction by measuring respective intensities of side lobes at different angles in the spectrum in order to determine a dimension of the feature.

20. The apparatus according to claim 19, and comprising collimating optics, which are adapted to collimate the beam of X-rays that is to impinge on the sample.

21. The apparatus according to claim 19, wherein the X-ray source is adapted to direct the beam to impinge on the surface at a grazing angle, and wherein the detector is positioned to detect a variation in the scattered X-rays associated with total external reflection from the area of the surface.

22. The apparatus according to claim 21, wherein the periodic feature comprises a layer having a first critical angle formed over a substrate having a second critical angle, and wherein the X-ray source is adapted to direct the beam at an angle between the first and second critical angles.

23. The apparatus according to claim 22, wherein the layer comprises an organic material, and the substrate comprises at least one of a metal, a semiconductor and a dielectric material.

24. The apparatus according to claim 19, wherein the feature comprises a pattern of parallel linear elements, and wherein the signal processor is adapted to measure a separation between side lobes in the spectrum in order to determine a spacing between the parallel lines.

25. The apparatus according to claim 19, wherein the feature comprises sidewalls, which are overlaid with a thin film, and wherein the signal processor is adapted to measure a thickness of the thin film on the sidewalls based on the spectrum.

26. The apparatus according to claim 19, wherein the sample comprises a semiconductor wafer.

27. The apparatus according to claim 26, wherein the periodic feature comprises photoresist deposited on the surface.

28. The apparatus according to claim 19, wherein the signal processor is adapted to analyze a modulation of the intensities of the side lobes as a function of angle.

29. Apparatus for X-ray analysis of a planar sample that includes a feature having sidewalls perpendicular to a plane of the sample, the sidewalls having a thin film thereon, the apparatus comprising:
- an X-ray source, which is adapted to direct a beam of X-rays to impinge on an area of the sample containing the feature;
- a detector, which is adapted to detect a spectrum of the X-rays scattered from the sample due to the feature; and
- a signal processor, which is adapted to analyze the spectrum to measure a characteristic of the thin film that is specific to the sidewalls.

30. The apparatus according to claim 29, and comprising collimating optics, which are adapted to collimate the beam of X-rays that is to impinge on the surface.

31. The apparatus according to claim 29, wherein the X-ray source is adapted to direct the beam to impinge on the surface at a grazing angle, and wherein the detector is positioned to detect a variation in the scattered X-rays associated with total external reflection from the area of the surface.

32. The apparatus according to claim 29, wherein the feature comprises a periodic pattern, and wherein the spectrum of the X-rays that is analyzed by the signal processor comprises a diffraction spectrum due to the periodic pattern.

33. The apparatus according to claim 32, wherein the diffraction spectrum comprises multiple side lobes, and wherein the signal processor is adapted to measure the characteristic by observing a modulation of the side lobes as a function of angle.

34. The apparatus according to claim 33, wherein the signal processor is adapted to determine a thickness of the thin film responsively to an angular spacing of the side lobes.

35. The apparatus according to claim 29, wherein the sample comprises a semiconductor wafer.

36. The apparatus according to claim 35, wherein the thin film comprises a barrier layer.

37. A cluster tool for producing microelectronic devices, comprising:
- a fabrication station, which is adapted to form a periodic feature on a surface of a semiconductor wafer; and
- an inspection station, comprising:
  - an X-ray source, which is adapted to direct a beam of X-rays to impinge on an area of the surface containing the periodic feature;
  - a detector, which is adapted to receive the X-rays scattered from the surface in a reflection mode so as to detect a spectrum of diffraction in the scattered X-rays as a function of azimuth; and
  - a signal processor, which is adapted to analyze the spectrum of diffraction by measuring respective intensities of side lobes at different angles in the spectrum in order to determine a dimension of the feature.

38. The cluster tool according to claim 37, wherein the periodic feature comprises sidewalls, which are overlaid with a thin film, and wherein the signal processor is adapted to measure a thickness of the thin film on the sidewalls based on the spectrum.

39. Apparatus for producing microelectronic devices, comprising:
- a production chamber, which is adapted to receive a semiconductor wafer;
- a fabrication device, which is adapted to form a periodic feature on a surface of the semiconductor wafer within the chamber;
- an X-ray source, which is adapted to direct a beam of X-rays toward the semiconductor wafer in the production chamber so as to impinge on an area of the surface containing the periodic feature;
- a detector, which is adapted to receive the X-rays scattered from the surface in a reflection mode so as to detect a spectrum of diffraction in the scattered X-rays as a function of azimuth; and
- a signal processor, which is adapted to analyze the spectrum of diffraction by measuring respective intensities of side lobes at different angles in the spectrum in order to determine a dimension of the feature.

40. The apparatus according to claim 39, wherein the periodic feature comprises sidewalls, which are overlaid with a thin film, and wherein the signal processor is adapted to measure a thickness of the thin film on the sidewalls based on the spectrum.

* * * * *